(12) United States Patent
Flockerzi

(10) Patent No.: US 7,671,068 B2
(45) Date of Patent: *Mar. 2, 2010

(54) N-(ALKOXYALKYL) CARBAMOYL-SUBSTITUTED 6-PHENYL-BENZONAPHTHYRIDINE DERIVATIVES AND THEIR USE AS PDE ¾ INHIBITORS

(75) Inventor: Dieter Flockerzi, Allensbach (DE)

(73) Assignee: NYCOMED GmbH, Konstanz (DE)

( * ) Notice: Subject to any disclaimer, the term of this patent is extended or adjusted under 35 U.S.C. 154(b) by 466 days.

This patent is subject to a terminal disclaimer.

(21) Appl. No.: 10/591,955

(22) PCT Filed: Mar. 16, 2005

(86) PCT No.: PCT/EP2005/051204

§ 371 (c)(1),
(2), (4) Date: Sep. 8, 2006

(87) PCT Pub. No.: WO2005/090345

PCT Pub. Date: Sep. 29, 2005

(65) Prior Publication Data

US 2007/0208051 A1    Sep. 6, 2007

(30) Foreign Application Priority Data

Mar. 17, 2004 (EP) .................... 04101101
Mar. 18, 2004 (EP) .................... 04101111

(51) Int. Cl.
| A01N 43/42 | (2006.01) |
| A61K 31/44 | (2006.01) |
| C07D 221/18 | (2006.01) |
| C07D 221/22 | (2006.01) |
| C07D 471/00 | (2006.01) |
| C07D 491/00 | (2006.01) |
| C07D 498/00 | (2006.01) |
| C07D 513/00 | (2006.01) |
| C07D 515/00 | (2006.01) |

(52) U.S. Cl. .................... 514/291; 514/279; 514/282; 546/42; 546/81

(58) Field of Classification Search .................. 514/282, 514/279, 291; 546/42, 81
See application file for complete search history.

(56) References Cited

U.S. PATENT DOCUMENTS

| 6,008,215 A | 12/1999 | Flockerzi |
| 6,143,759 A | 11/2000 | Flockerzi |
| 6,306,869 B1 | 10/2001 | Flockerzi |
| 6,436,952 B1 | 8/2002 | Flockerzi |
| 2006/0113968 A1 | 6/2006 | Flockerzi |

FOREIGN PATENT DOCUMENTS

| WO | 98/21208 A1 | 5/1998 |
| WO | WO 98/21208 * | 5/1998 |
| WO | 98/40382 A1 | 9/1998 |
| WO | 99/57118 A1 | 11/1999 |
| WO | 00/12501 A1 | 3/2000 |
| WO | 02/066476 A1 | 8/2002 |

* cited by examiner

*Primary Examiner*—Shengjun Wang
*Assistant Examiner*—Sarah Pihonak
(74) *Attorney, Agent, or Firm*—The Nath Law Group; Joshua B. Goldberg; Sheldon M. McGee

(57) ABSTRACT

Compounds of the formula I (1)

in which the substitutents have the definitions provided in the specification, are novel, effective PDE 3/4 inhibitors.

6 Claims, No Drawings

N-(ALKOXYALKYL) CARBAMOYL-SUBSTITUTED 6-PHENYL-BENZONAPHTHYRIDINE DERIVATIVES AND THEIR USE AS PDE ¾ INHIBITORS

This application was filed under 35 U.S.C. 371 as a national stage of PCT/EP2005/051204, filed March 16, 2005.

FIELD OF APPLICATION OF THE INVENTION

The invention relates to novel 6-phenylbenzonaphthyridines which are used in the pharmaceutical industry for the production of pharmaceutical compositions.

KNOWN TECHNICAL BACKGROUND

The international applications WO98/21208 (=U.S. Pat. No. 6,008,215), WO98/40382 (=U.S. Pat. No. 6,143,759), WO99/57118 (=U.S. Pat. No. 6,306,869), W00/12501 and WO02/066476 describe 6-phenylbenzonaphthyridines and their N-oxides as PDE3/4 inhibitors.

DESCRIPTION OF THE INVENTION

It has now been found that the compounds of formula 1, which are described in more detail below and which differ from the prior-art compounds in particular by substitution on the 6-phenyl ring, have surprising and particularly advantageous properties.

The invention thus relates to compounds of formula 1,

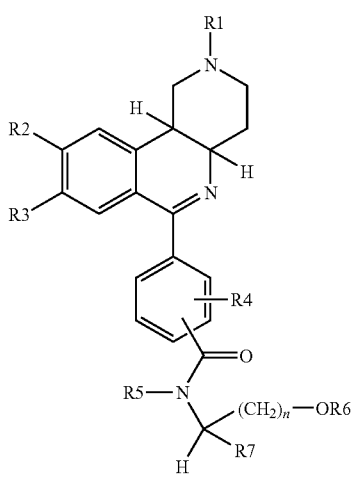

(1)

in which
R1 is 1-4C-alkyl,
R2 is hydroxyl, 1-4C-alkoxy, 3-7C-cycloalkoxy, 3-7C-cycloalkylmethoxy, or 1-4C-alkoxy which is completely or predominantly substituted by fluorine,
R3 is hydroxyl, 1-4C-alkoxy, 3-7C-cycloalkoxy, 3-7C-cycloalkylmethoxy, or 1-4C-alkoxy which is completely or predominantly substituted by fluorine, or in which
R2 and R3 together are a 1-2C-alkylenedioxy group,
R4 is hydrogen, halogen, nitro, 1-4C-alkyl, trifluoromethyl or 1-4C-alkoxy,
R5 is hydrogen, 1-8C-alkyl, 3-7C-cycloalkyl or phenyl-1-4C-alkyl,
R6 is 1-4C-alkyl, phenyl-1-4C-alkyl, or Aryl-1-4C-alkyl, in which
Aryl is R61- and/or R62-substituted phenyl, in which
R61 is 1-4C-alkoxy, trifluoromethyl or cyano,
R62 is 1-4C-alkoxy, and in which either
R7 is 1-4C-alkyl, and
n is 1 or 2, or
R7 is hydrogen, and
n is 1, 2 or 3, the salts, the N-oxides of these compounds and the salts of the latter.

1-4C-Alkyl represents a straight-chain or branched alkyl radical having 1 to 4 carbon atoms. Examples which may be mentioned are the butyl, isobutyl, sec-butyl, tert-butyl, propyl, isopropyl and, preferably, the ethyl and methyl radicals.

1-4C-Alkoxy represents radicals which, in addition to the oxygen atom, contain a straight-chain or branched alkyl radical having 1 to 4 carbon atoms. Examples which may be mentioned are the butoxy, isobutoxy, sec-butoxy, tert-butoxy, propoxy, isopropoxy and, preferably, the ethoxy and methoxy radicals.

3-7C-Cycloalkoxy represents, for example, cyclopropyloxy, cyclobutyloxy, cyclopentyloxy, cyclohexyloxy and cycloheptyloxy, of which cyclopropyloxy, cyclobutyloxy and cyclopentyloxy are preferred.

3-7C-Cycloalkylmethoxy represents, for example, cyclopropylmethoxy, cyclobutylmethoxy, cyclopentylmethoxy, cyclohexylmethoxy and cycloheptylmethoxy, of which cyclopropylmethoxy, cyclobutylmethoxy and cyclopentylmethoxy are preferred.

As 1-4C-Alkoxy which is completely or predominantly substituted by fluorine, the 2,2,3,3,3-pentafluoropropoxy, the perfluoroethoxy, the 1,1,2,2-tetrafluoroethoxy, the 1,2,2-trifluoroethoxy, the trifluoro-methoxy, in particular the 2,2,2-trifluoroethoxy, and preferably the difluoromethoxy radicals, for example, may be mentioned. In this context, "predominantly" means that more than half of the hydrogen atoms of the 1-4C-alkoxy groups are replaced by fluorine atoms.

1-2C-Alkylenedioxy represents, for example, the methylenedioxy (—O—CH$_2$—O—) or the ethylenedioxy (—O—CH$_2$—CH$_2$—O—) radical.

Halogen within the meaning of the invention is fluorine, chlorine or bromine.

1-8C-Alkyl represents straight-chain or branched alkyl radicals having 1 to 8 carbon atoms. Examples which may be mentioned are the octyl, heptyl, isoheptyl (5-methylhexyl), hexyl, isohexyl (4-methyl-pentyl), neohexyl (3,3-dimethylbutyl), pentyl, isopentyl (3-methylbutyl), neopentyl (2,2-dimethylpropyl), butyl, isobutyl, sec-butyl, tert-butyl, propyl, isopropyl, ethyl or methyl radical.

3-7C-Cycloalkyl represents the cyclopropyl, cyclobutyl, cyclopentyl, cyclohexyl or cycloheptyl radical.

Phenyl-1-4C-alkyl represents one of the abovementioned 1-4C-alkyl radicals which is substituted by phenyl. As examples may be mentioned the benzyl, phenethyl or 3-phenylpropyl radicals.

Aryl-1-4C-alkyl represents one of the abovementioned 1-4C-alkyl radicals which is substituted by Aryl. As examples may be mentioned the 2-Arylethyl or, in particular, the Arylmethyl radical.

Aryl represents R61- and/or R62-substituted phenyl.

"N-oxides of these compounds" stands for any single or multiple N-oxide(s), which can be formed starting from the compounds of formula 1. Preferred are the single N-oxides at the nitrogen atom in 2-position of the benzonaphthyridine ring system.

The substitutents R4 and —C(O)N(R5)-C(R7)H—(CH$_2$)$_n$—OR6 of the compounds of formula 1 can be attached in the ortho, meta or para position with respect to the binding position in which the 6-phenyl ring is bonded to the benzonaphthyridine ring system. Preference is given to compounds of formula 1, in which R4 is hydrogen and —C(O)N(R5)-C(R7)H—(CH$_2$)$_n$—OR6 is attached in the meta or in the para position; most preferred is the para position.

The substitutents R61 and/or R62 of the compounds of formula 1 can be attached in the ortho, meta or para position with respect to the binding position in which the phenyl ring is bonded to the 1-4C-alkyl moiety. Preference is given to the attachment in the meta or in the para position.

Suitable salts of compounds of formula 1—depending on substitution—are all acid addition salts or all salts with bases. The pharmacologically tolerable salts of the inorganic and organic acids and bases customarily used in pharmacy may be particularly mentioned. Those suitable are, on the one hand, water-soluble and water-insoluble acid addition salts with acids such as, for example, hydrochloric acid, hydrobromic acid, phosphoric acid, nitric acid, sulfuric acid, acetic acid, citric acid, D-gluconic acid, benzoic acid, 2-(4-hydroxybenzoyl)benzoic acid, butyric acid, sulfosalicylic acid, maleic acid, lauric acid, malic acid, fumaric acid, 2-hydroxy-succinic acid, succinic acid, oxalic acid, tartaric acid, embonic acid, stearic acid, toluenesulfonic acid, methanesulfonic acid or 3-hydroxy-2-naphthoic acid, where the acids are employed in salt preparation—depending on whether a mono- or polybasic add is concerned and depending on which salt is desired—in an equimolar quantitative ratio or one differing therefrom.

On the other hand salts with bases are also suitable. Examples of salts with bases which may be mentioned are alkali metal (lithium, sodium, potassium) or calcium, aluminum, magnesium or titanium salts, where here too the bases are employed in salt preparation in an equimolar quantitative ratio or one differing therefrom.

Pharmacologically intolerable salts which can be obtained first, for example, as process products in the preparation of the compounds according to the invention on an industrial scale, are converted into pharmacologically tolerable salts by methods known to the person skilled in the art.

It is known to the person skilled in the art that the compounds according to the invention and their salts, for example when they are isolated in crystalline form, may comprise varying amounts of solvents. Accordingly, the invention also embraces all solvates and in particular all hydrates of the compounds of formula 1, and also all solvates and in particular all hydrates of the salts of the compounds of formula 1.

Compounds of formula 1 more worthy to be mentioned are those in which
R1 is 1-4C-alkyl,
R2 is 1-2C-alkoxy, 3-5C-cycloalkoxy, 3-5C-cycloalkylmethoxy, or 1-2C-alkoxy which is completely or predominantly substituted by fluorine,
R3 is 1-2C-alkoxy, 3-5C-cycloalkoxy, 3-5C-cycloalkylmethoxy, or 1-2C-alkoxy which is completely or predominantly substituted by fluorine,
R4 is hydrogen, 1-4C-alkyl, trifluoromethyl or 1-4C-alkoxy,
R5 is hydrogen, 1-4C-alkyl, 3-7C-cycloalkyl or phenyl-1-4C-alkyl,
R6 is 1-4C-alkyl, phenyl-1-4C-alkyl, or Aryl-1-4C-alkyl, in which
Aryl is R61- and/or R62-substituted phenyl, in which
R61 is 1-4C-alkoxy, trifluoromethyl or cyano,
R62 is 1-4C-alkoxy,
R7 is hydrogen or 1-4C-alkyl,
n is 1 or 2, the salts, the N-oxides of these compounds and the salts of the latter.

Compounds of formula 1 in particular worthy to be mentioned are those in which
R1 is methyl,
R2 is 1-2C-alkoxy,
R3 is 1-2C-alkoxy,
R4 is hydrogen,
R5 is hydrogen, 1-4C-alkyl, 3-7C-cycloalkyl or phenyl-1-4C-alkyl,
R6 is 1-4C-alkyl, phenyl-1-4C-alkyl, or Aryl-1-4C-alkyl, in which
Aryl is 1-4C-alkoxy-substituted phenyl, trifluoromethyl-substituted phenyl, cyano-substituted phenyl, or R61- and R62-substituted phenyl, in which
R61 is 1-4C-alkoxy,
R62 is 1-4C-alkoxy,
R7 is hydrogen or 1-4C-alkyl,
n is 1 or 2, the salts, the N-oxides of these compounds and the salts of the latter.

Compounds of formula 1 in more particular worthy to be mentioned are those in which
R1 is methyl,
R2 is ethoxy,
R3 is methoxy,
R4 is hydrogen,
R5 is hydrogen, methyl, ethyl, propyl, isopropyl, cyclohexyl or benzyl,
R6 is methyl, ethyl, isopropyl, butyl, benzyl, 3-phenylpropyl, or Aryl-methyl, in which
Aryl is 4-methoxyphenyl, 4-trifluoromethylphenyl, 4-cyanophenyl or 3,5-dimethoxyphenyl,
R7 is hydrogen, methyl, ethyl or isobutyl,
n is 1 or 2, the salts, the N-oxides of these compounds and the salts of the latter.

Compounds of formula 1 in still more particular worthy to be mentioned are those in which
R1 is methyl,
R2 is ethoxy,
R3 is methoxy,
R4 is hydrogen,
R5 is hydrogen, methyl, ethyl, propyl, isopropyl, cyclohexyl or benzyl,
R6 is methyl, ethyl, isopropyl, butyl, benzyl, 3-phenylpropyl, or Aryl-methyl, in which
Aryl is 4-methoxyphenyl, 4-trifluoromethylphenyl, 4-cyanophenyl or 3,5-dimethoxyphenyl, and in which either
R7 is hydrogen or methyl, and
n is 1 or 2, or R7 is ethyl or isobutyl, and
n is 1, the salts, the N-oxides of these compounds and the salts of the latter.

A special embodiment of the compounds of the present invention include those compounds of formula 1, in which R1 is methyl, R2 is ethoxy and R3 is methoxy.

Another special embodiment of the compounds of the present invention include those compounds of formula 1 in which R1 is methyl, R2 is ethoxy, R3 is methoxy and R4 is hydrogen.

Still another special embodiment of the compounds of the present invention include those compounds of formula 1 in which R1 is methyl, R2 is ethoxy, R3 is methoxy, R4 is hydrogen and the radical —C(O)N(R5)-C(R7)H—(CH$_2$)$_n$—OR6 is attached to the 6-phenyl-ring in para-position.

The compounds of formula 1 are chiral compounds having chiral centers in positions 4a and 10b as well as, depending of the meaning of R7, in the radical —C(O)N(R5)-C(R7)H—(CH$_2$)$_n$—OR6.

Numbering:

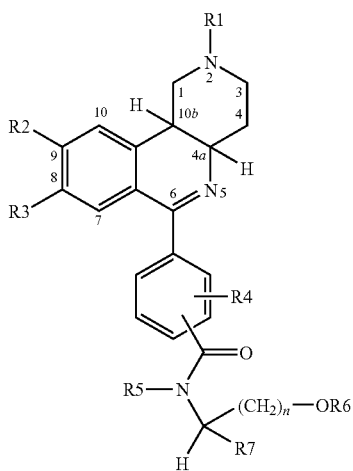

(1)

The invention therefore includes all conceivable pure diastereomers and pure enantiomers and mixtures thereof in any mixing ratio, including the racemates. Preference is given to compounds of formula 1 in which the hydrogen atoms in positions 4a and 10b are in the cis position relative to one another. The pure cis enantiomers and their mixtures in any mixing ratio and including the racemates are particularly preferred.

In particular preferred compounds in this context are those compounds of formula 1, which have with respect to the chiral centers the configuration shown in formulae (1*) and (1**):

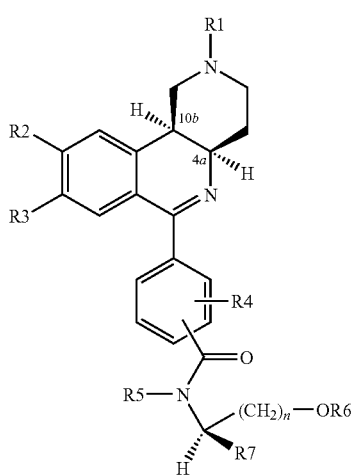

(1*)

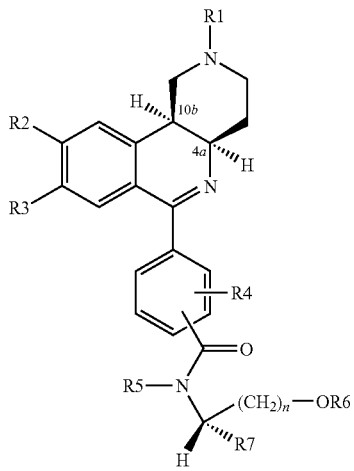

(1**)

The compounds according to the invention can be prepared, for example, as shown in the reaction scheme 1 and as described below, as described in the following examples or analogously or similarly thereto.

The compounds of formula 1 can be prepared by reacting compounds of formula 4, in which R1, R2, R3 and R4 have the meanings given above, with compounds of formula 2, in which R5, R6, R7 and n have the meanings given above.

Advantageously, the reaction is carried out using standard coupling reagents known to the person skilled in the art, such as, for example, N,N'-dicyclohexylcarbodiimide, N'-(3-dimethylaminopropyl)-N-ethylcarbodiimide or O-Benzotriazol-1-yl-N,N,N',N'-bis-(tetramethylen)-uronium-hexafluorophosphat.

Alternatively, the compounds of formula 4, in which R1, R2, R3 and R4 have the meanings given above can in a first step be activated, for example by forming an acid halide or acid anhydride (compounds of formula 3; Y is for example halogen, preferably chlorine) and in a second step be reacted with compounds of formula 2, in which R5, R6, R7 and n have the meanings given above, to yield the compounds of formula 1.

Compounds of formula 2 are known or can be prepared according to processes known to the person skilled in the art starting from appropriate compounds known to the person skilled in the art. They can be prepared, for example, starting from commercial amino acids by N-alkylation via reductive amination of the appropriate ketone (such as e.g. described in Chemistry Letters 1984, p. 441-444), reduction of the N-alkyl-amino acids to N-alkyl-amino alcohols (such as e.g. described in Tetrahedron 45/16, 4969-4988 (1989)) and, finally, O-alkylation (such as e.g. described in Tetrahedron 45/16, 4969-4988 (1989)). Said reactions can be carried out in an art-known manner or analogously or similarly thereto.

The preparation of compounds of formulae 3 and 4 is described, for example, in the International Patent Applications WO98/21208 (=U.S. Pat. No. 6,008,215) and WO02/066476.

Compounds of formulae (1*) and (1**) can be prepared by reacting (4aR, 10bS)-configurated compounds of formulae 3 or 4 with enantiomeric pure compounds of formula 2. The preparation of (4aR, 10bS)-configurated compounds of formulae 3 and 4 is also described in the International Patent Applications WO98/21208 (=U.S. Pat. No. 6,008,215) and WO02/066476. The preparation of enantiomeric pure compounds of formula 2 is known to the person skilled in the art; they can be prepared, for example, starting from art-known starting compounds, such as e.g. 2R-amino-propanol, 2S-amino-propanol, 3R-amino-butanol or 3S-amino-butanol, or as described above starting from enantiomeric pure amino adds.

Reaction scheme 1:

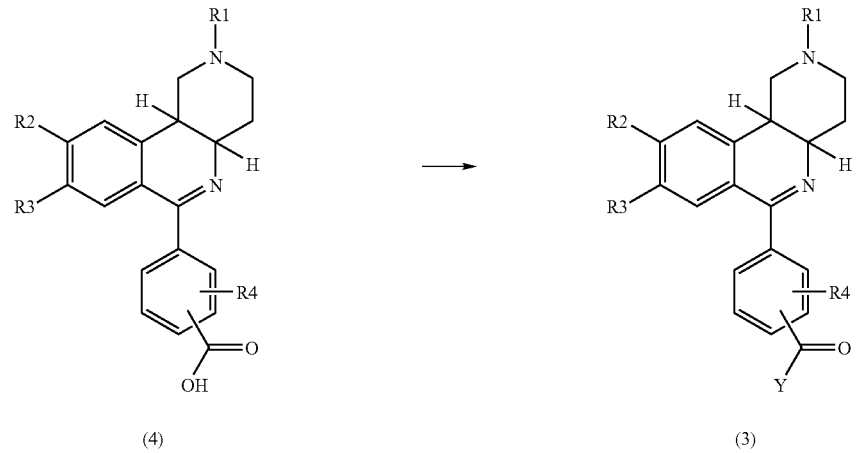

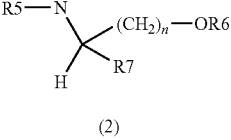

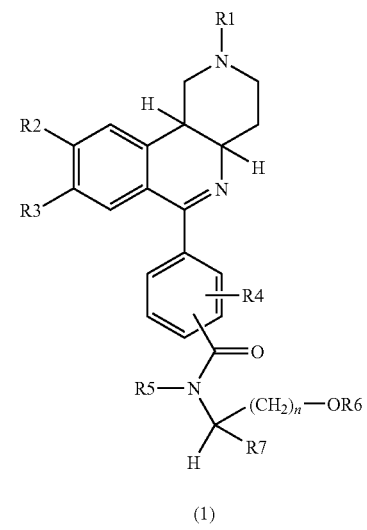

The compounds of formula 1 prepared by the processes described above can, if desired, be converted into their salts, or salts of the compounds of formula 1 obtained can, if desired, be converted into the free compounds. Corresponding processes are known to the person skilled in the art.

In addition, the compounds of formula 1 can be converted by derivatisation into further compounds of formula 1. Thus, for example, compounds of formula 1 can be converted, if desired, into their N-oxides.

The N-oxidation is carried out in a manner, which is known to the person skilled in the art, for example with the aid of hydrogen peroxide in methanol or with the aid of m-chloroperoxybenzoic acid in dichloromethane. The person skilled in the art is familiar on the basis of his/her expert knowledge with the reaction conditions, which are specifically necessary for carrying out the N-oxidation.

It is also known to the person skilled in the art that, if a plurality of reactive centers are present in a starting material or intermediate, it may be necessary to temporarily block one or more reactive centers with protective groups so that a reaction takes place only at the desired reactive center. A detailed description of how to use a large number of proven protective groups can be found, for example, in T. W. Greene, Protective Groups in Organic Synthesis, John Wiley & Sons, 1991 or 1999 (3$^{rd}$ edition).

The substances according to the invention are isolated and purified in a manner known per se, for example by distilling off the solvent under reduced pressure and recrystallizing the residue obtained from a suitable solvent or subjecting it to one of the customary purification methods, such as, for example, column chromatography on a suitable support material.

Salts are obtained by dissolving the free compound in a suitable solvent (e.g. a ketone, such as acetone, methyl ethyl ketone or methyl isobutyl ketone, an ether, such as diethyl ether, tetrahydrofuran or dioxane, a chlorinated hydrocarbon, such as methylene chloride or chloroform, or a low-molecular-weight aliphatic alcohol, such as ethanol or isopropanol) which contains the desired acid or base, or to which the desired acid or base is then added. The salts are obtained by filtering, reprecipitating, precipitating with a nonsolvent for the addition salt or by evaporating the solvent. Salts obtained can be converted into the free compounds, which can in turn be converted into salts, by alkalization or by acidification. In this manner, pharmacologically unacceptable salts can be converted into pharmacologically acceptable salts.

The following examples serve to illustrate the invention in greater detail without restricting it. Further compounds of formula 1, whose preparation is not explicitly described, can also be prepared in an analogous manner or in a manner familiar per se to the person skilled in the art using customary process techniques.

In the examples, m.p. stands for melting point, h for hour(s), RT for room temperature, calc for calculated and fnd for found The compounds mentioned in the examples as end products and their salts are a preferred subject of the invention.

EXAMPLES

End Products 1. 4-(4aR,10bS)-9-Ethoxy-8-methoxy-2-methyl-1,2,3,4,4a,10b-hexahydro-benzo[c][1,6]naphthyridin-6-yl)-N-(3-isopropoxy-propyl)-benzamide; hydrochloride

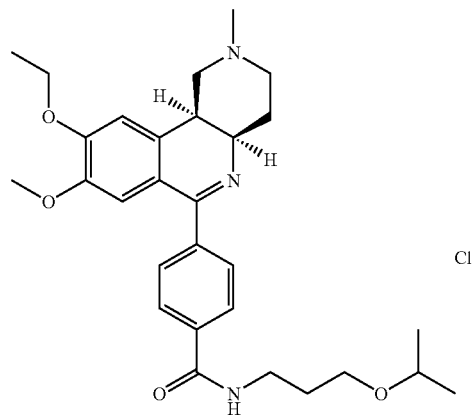

1,4 ml of N,N-Diisopropyl-ethyl amine are added to a suspension of 0.79 g 4-((4aR,10bS)-9-ethoxy-8-methoxy-2-methyl-1,2,3,4,4a,10b-hexahydrobenzo[c][1,6]naphthyridin-6-yl)benzoic acid and 0.24 g of 3-isopropoxypropyl-amine in 20 ml of dichloromethane. The reaction mixture is stirred at RT for 10 min and then 0.91 g of O-Benzotriazol-1-yl-N,N,N',N'-bis-(tetramethylen)-uronium-hexafluorophosphate (HBTU) are added, yielding a clear light-brown solution. The reaction mixture is stirred at RT for about 15 h and filtered. The filtrate is substantially concentrated under reduced pressure, and the highly viscous residue is partitioned between dichloromethane and saturated sodium bicarbonate solution. The organic phase is washed with water, dried over sodium sulfate and concentrated. The resin-like residue is purified by silica gel chromatography, and the product fraction is separated off and concentrated. The viscous residue is treated with 1 equivalent of etheric HCl yielding 0.80 g of the title compound as a solid foam.

MS: calc.: $C_{28}H_{40}N_3O_4$ (493.65) fnd.: [M+1] 494.2

Analogously to example 1, the following title compounds are obtained when, instead of 3-isopropoxypropyl-amine, the respective appropriately substituted amines are used as reaction partner:

2. 4-((4aR,10bS)-9-Ethoxy-8-methoxy-2-methyl-1,2,3,4,4a,10b-hexahydro-benzo [c][1,6]naphthyridin-6-yl)-N-((S)-2-methoxy-1-methyl-ethyl)-benzamide; hydrochloride

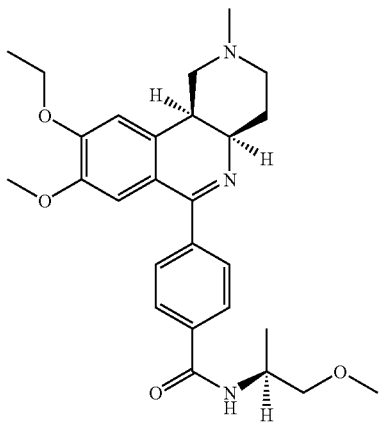

Prepared from 4-((4aR,10bS)-9-ethoxy-8-methoxy-2-methyl-1,2,3,4,4a,10b-hexahydro-benzo[c][1,6]naphthyridin-6-yl)benzoic acid and (S)-2-methoxy-1-methyl-ethyl-amine as described for example 1.

MS: calc.: $C_{27}H_{35}N_3O_4$ (465.60) fnd.: [M+1] 466.2

3. 4-((4aR,10bS)-9-Ethoxy-8-methoxy-2-methyl-1,2,3,4,4a,10b-hexahydro-benzo [c][1,6]naphthyridin-6-yl)-N-(1(rac)-methoxymethyl-propyl)-benzamide; hydrochloride

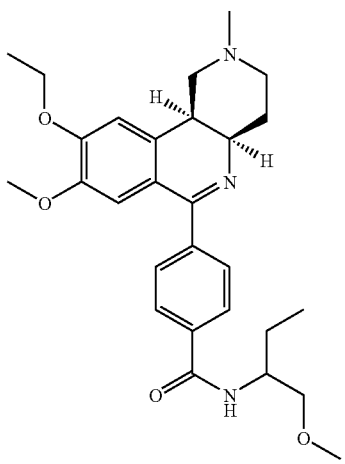

Prepared from 4-((4aR,10bS)-9-ethoxy-8-methoxy-2-methyl-1,2,3,4,4a,10b-hexahydro-benzo[c][1,6]naphthyridin-6-yl)benzoic acid and (rac)-1-methoxymethyl-propyl-amine as described for example 1.

MS: calc.: $C_{28}H_{37}N_3O_4$ (479.62) fnd.: [M+1] 480

4. 4-((4aR,10bS)-9-Ethoxy-8-methoxy-2-methyl-1,2,3,4,4a,10b-hexahydro-benzo [c][1,6]naphthyridin-6-yl)-N-(3-ethoxy-propyl)-benzamide; hydrochloride

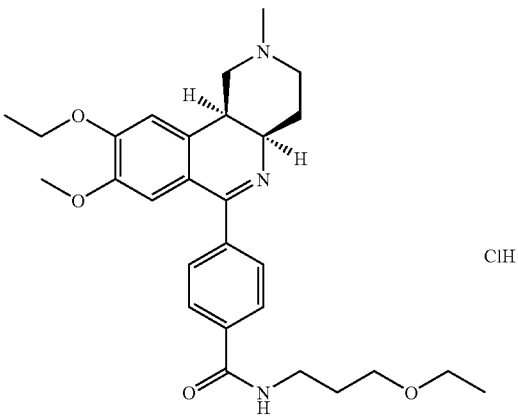

Prepared from 4-((4aR,10bS)-9-ethoxy-8-methoxy-2-methyl-1,2,3,4,4a,10b-hexahydro-benzo[c][1,6]naphthyridin-6-yl)benzoic acid and 3-ethoxy-propyl-amine as described for example 1.

MS: calc.: $C_{28}H_{37}N_3O_4$ (479.62) fnd.: [M+1] 480.2

5. 4-((4aR,10bS)-9-Ethoxy-8-methoxy-2-methyl-1,2,3,4,4a,10b-hexahydro-benzo [c][1,6]naphthyridin-6-yl)-N-ethyl-N-(2-methoxy-ethyl)-benzamide; hydrochloride

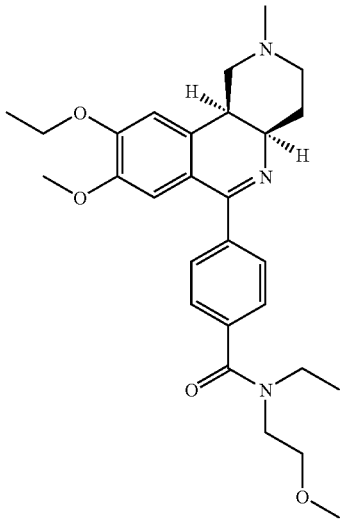

Prepared from 4-((4aR,10bS)-9-ethoxy-8-methoxy-2-methyl-1,2,3,4,4a,10b-hexahydro-benzo[c][1,6]naphthyridin-6-yl)benzoic acid and N-2-methoxyethyl-N-ethyl-amine as described for example 1.

MS: calc.: $C_{28}H_{37}N_3O_4$ (479.62) fnd.: [M+1] 480.2

6. 4-((4aR,10bS)-9-Ethoxy-8-methoxy-2-methyl-1,2,3,4,4a,10b-hexahydro-benzo [c][1,6]naphtpyridin-6-yl)-N-(2-methoxy-ethyl)-N-propyl-benzamide; hydrochloride

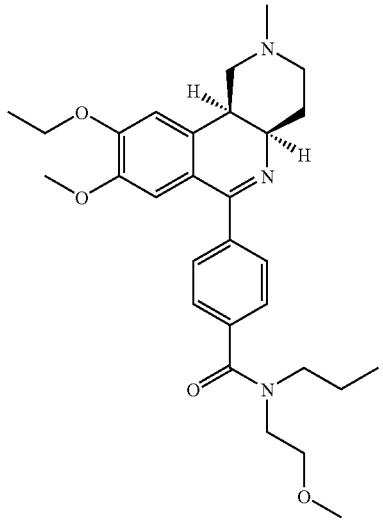

Prepared from 4-((4aR,10bS)-9-ethoxy-8-methoxy-2-methyl-1,2,3,4,4a,10b-hexahydro-benzo[c][1,6]naphthyridin-6-yl)benzoic acid and N-2-methoxy-ethyl-N-propyl-amine as described for example 1.

MS: calc.: $C_{29}H_{39}N_3O_4$ (493.65) fnd.: [M+1] 494.8

7. 4-((4aR,10bS)-9-Ethoxy-8-methoxy-2-methyl-1,2,3,4,4a,10b-hexahydro-benzo [c][1,6]naphthyridin-6-yl)-N-isopropyl-N-(2-methoxy-ethyl)-benzamide; hydrochloride

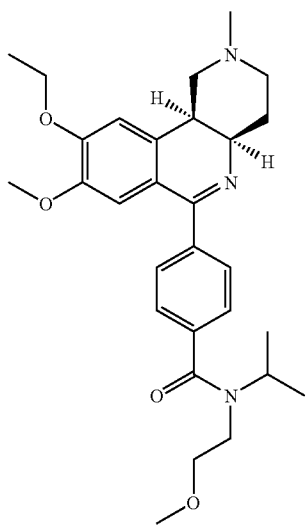

Prepared from 4-((4aR,10bS)-9-ethoxy-8-methoxy-2-methyl-1,2,3,4,4a,10b-hexahydro-benzo[c][1,6]naphthyridin-6-yl)benzoic acid and N-isopropyl-N-(2-methoxy-ethyl)-amine as described for example 1.

MS: calc.: $C_{29}H_{39}N_3O_4$ (493.65) fnd.: [M+1] 494.6

8. N—((R)-2-Benzyloxy-1-methyl-ethyl)-4-((4aR,10bS)-9-ethoxy-8-methoxy-2-methyl-1,2,3,4,4a,10b-hexahydro-benzo[c][1,6]naphthyridin-6-yl)-N-isopropyl-benzamide

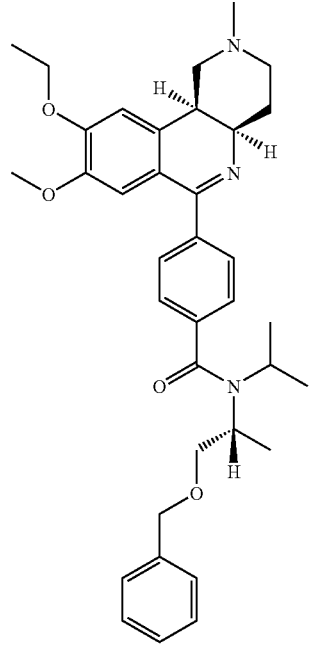

Prepared from 4-((4aR,10bS)-9-ethoxy-8-methoxy-2-methyl-1,2,3,4,4a,10b-hexahydro-benzo[c][1,6]naphthyridin-6-yl)benzoic acid and ((R)-2-benzyloxy-1-methyl-ethyl)-isopropyl-amine as described for example 1.

MS: calc.: $C_{36}H_{45}N_3O_4$ (583.78) fnd.: [M+1] 584.8

9. N—((S)-2-Benzyloxy-1-methylethyl)-4-((4aR,10bS)-9-ethoxy-8-methoxy-2-methyl-1,2,3,4,4a,10b-hexahydro-benzo[c][1,6]naphthyridin-6-yl)-N-isopropyl-benzamide

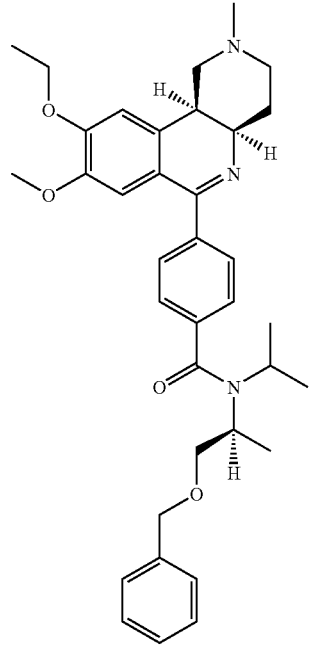

Over a period of about 5 min, a solution of 0.42 g of 4-((4aR,10bS-9-ethoxy-8-methoxy-2-methyl-1,2,3,4,4a,10b-hexahydrobenzo[c][1,6]naphthyridin-6-yl)benzoyl chloride in 10 ml of acetonitrile is added dropwise to a mixture, cooled with ice/water, of 0.110 g of ((R)-2-benzyloxy-1-methyl-ethyl)-isopropyl-amine hydrochloride and 0.5 g of triethylamine in 10 ml of acetonitrile. The reaction mixture is stirred at RT for about 15 h and then substantially concentrated under reduced pressure, and the highly viscous residue is partitioned between dichloromethane and saturated sodium bicarbonate solution. The organic phase is washed with water, dried over sodium sulfate and concentrated. The resin-like residue is purified by silica gel chromatography, and the product fraction is separated off and concentrated. This gives 0.34 g of the title compound as a solid foam.

MS: calc.: $C_{36}H_{45}N_3O_4$ (583.78) fnd.: [M+1] 584.6

10. N-(3-Benzyloxy-1-methyl-propyl)-4-((4aR,10bS)-9-ethoxy-8-methoxy-2-methyl-1,2,3,4,4a,10b-hexahydro-benzo[c][1,6]naphthyridin-6-yl)-N-isopropyl-benzamide

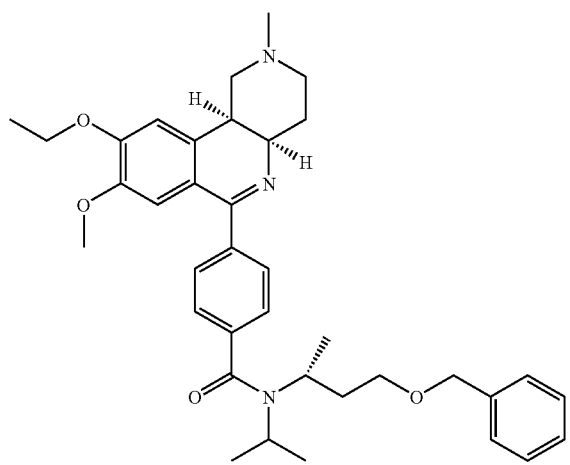

Prepared from 4-((4aR,10bS)-9-ethoxy-8-methoxy-2-methyl-1,2,3,4,4a,10b-hexahydro-benzo[c][1,6]naphthyridin-6-yl)benzoyl chloride and rac-N-(3-benzyloxy-1-methyl-propyl)-N-isopropyl-amine hydrochloride as described for example 9.

MS: calc.: $C_{37}H_{47}N_3O_4$ (597.80) fnd.: [M+1] 598.6

11. 4-((4aR,10bS)-9-Ethoxy-8-methoxy-2-methyl-1,2,3,4,4a,10b-hexahydro-benzo [c][1,6]naphthyridin-6-yl)-N-isopropyl-N-((S)-2-methoxy-1-methyl-ethyl)-benzamide; hydrochloride

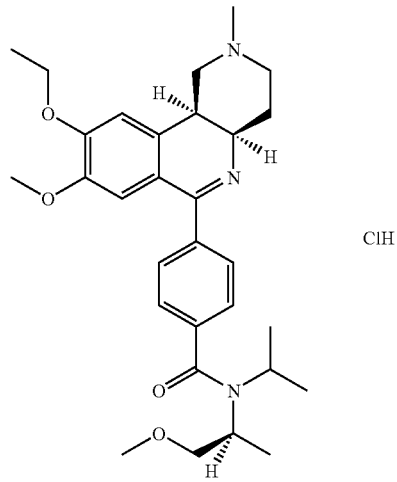

Prepared from 4-((4aR,10bS)-9-ethoxy-8-methoxy-2-methyl-1,2,3,4,4a,10b-hexahydro-benzo[c][1,6]naphthyridin-6-yl)benzoic acid and N-isopropyl-N-((S)-2-methoxy-1-methyl-ethyl-amine as described for example 1.

MS: calc.: $C_{30}H_{41}N_3O_4$ (507.68) fnd.: [M+1] 508.8

12. N-Cyclohexyl-4-((4aR,10bS)-9-ethoxy-8-methoxy-2-methyl-1,2,3,4,4a,10b-hexahydro-benzo [c][1,6]naphthyridin-6-yl)-N-(2-methoxy-ethyl)-benzamide; hydrochloride

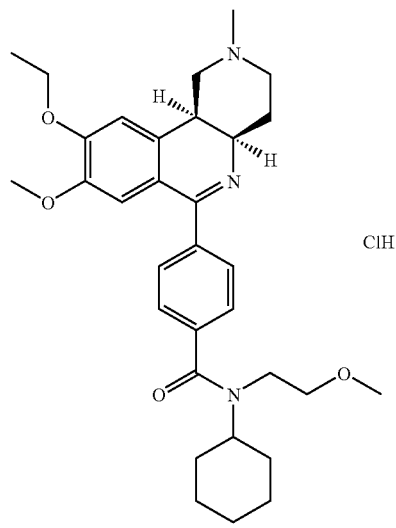

Prepared from 4-((4aR,10bS)-9-ethoxy-8-methoxy-2-methyl-1,2,3,4,4a,10b-hexahydro-benzo[c][1,6]naphthyridin-6-yl)benzoic acid and N-cyclohexyl-N-(2-methoxy-ethyl)-amine as described for example 1.

MS: calc.: $C_{32}H_{43}N_3O_4$ (533.72) fnd.: [M+1] 534.8

13. N-Cyclohexyl-4-((4aR,10bS)-9-ethoxy-8-methoxy-2-methyl-1,2,3,4,4a,10b-hexahydro-benzo [c][1,6]naphthyridin-6-yl)-N-(3-methoxy-propyl)-benzamide; hydrochloride

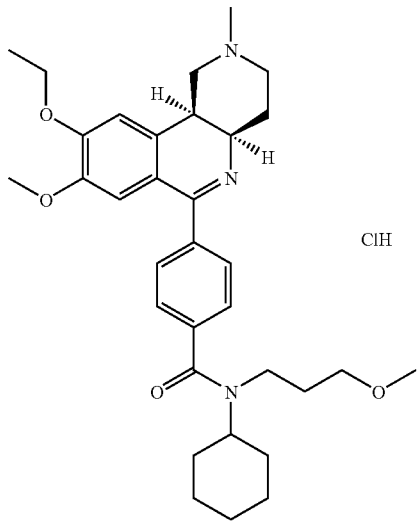

Prepared from 4-((4aR,10bS)-9-ethoxy-8-methoxy-2-methyl-1,2,3,4,4a,10b-hexahydro-benzo[c][1,6]naphthyridin-6-yl)benzoic acid and N-cyclohexyl-N-(2-methoxy-propyl)-amine as described for example 1.

MS: calc.: $C_{33}H_{45}N_3O_4$ (547.74) fnd.: [M+1] 548.6

14. 4-((4aR,10bS)-9-Ethoxy-8-methoxy-2-methyl-1,2,3,4,4a,10b-hexahydro-benzo [c][1,6]naphthyridin-6-yl)-N-(2-methoxy-ethyl)-benzamide; hydrochloride

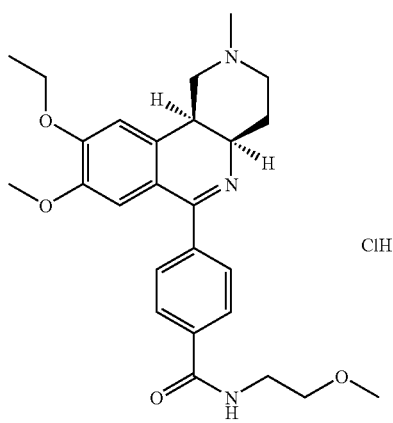

Prepared from 4-((4aR,10bS)-9-ethoxy-8-methoxy-2-methyl-1,2,3,4,4a,10b-hexahydro-benzo[c][1,6]naphthyridin-6-yl)benzoic acid and 2-methoxy-ethyl-amine as described for example 1.

MS: calc.: $C_{26}H_{32}N_3O_4$ (451.57) fnd.: [M+1] 452.8

15. 4-((4aR,10bS)-9-Ethoxy-8-methoxy-2-methyl-1,2,3,4,4a,10b-hexahydro-benzo [c][1,6]naphthyridin-6-yl)-N-(2-methoxy-ethyl)-N-methyl-benzamide; hydrochloride

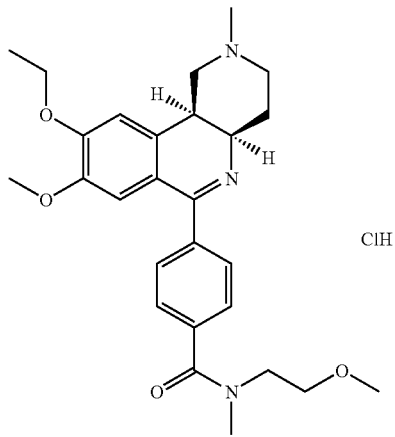

Prepared from 4-((4aR,10bS)-9-ethoxy-8-methoxy-2-methyl-1,2,3,4,4a,10b-hexahydro-benzo[c][1,6]naphthyridin-6-yl)benzoic acid and N-(2-methoxy-ethyl)-N-methyl-amine as described for example 1.

MS: calc.: $C_{27}H_{35}N_3O_4$ (465.60) fnd.: [M+1] 465.8

16. N-(3-Butoxy-propyl)-4-((4aR,10bS)-9-ethoxy-8-methoxy-2-methyl-1,2,3,4,4a,10b-hexahydro-benzo [c][1,6]naphthyridin-6-yl)-benzamide; hydrochloride

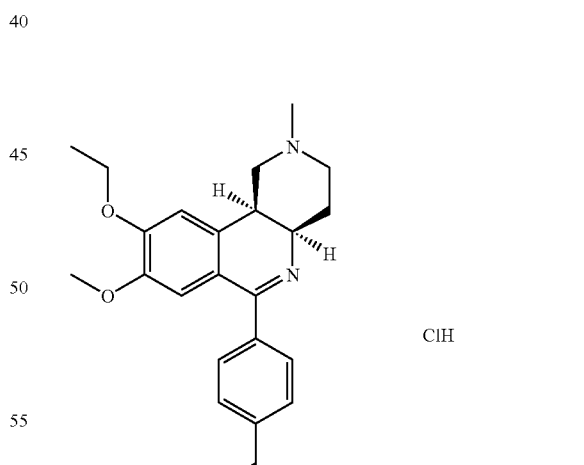

Prepared from 4-((4aR,10bS)-9-ethoxy-8-methoxy-2-methyl-1,2,3,4,4a,10b-hexahydro-benzo[c][1,6]naphthyridin-6-yl)benzoic acid and 3-butoxy-propyl-amine as described for example 1.

MS: calc.: $C_{30}H_{41}N_3O_4$ (507.68) fnd.: [M+1] 508.8

17. N—[(S)-2-(3,5-Dimethoxy-benzyloxy)-1-methyl-ethyl]-4-((4aR,10bS)-9-ethoxy-8-methoxy-2-methyl-1,2,3,4,4a,10b-hexahydro-benzo[c][1,6]naphthyridin-6-yl)-N-isopropyl-benzamide

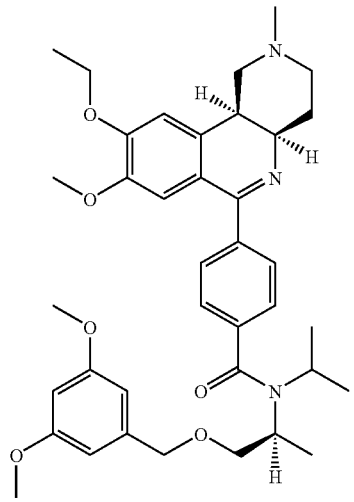

Prepared from 4-((4aR,10bS)-9-ethoxy-8-methoxy-2-methyl-1,2,3,4,4a,10b-hexahydro-benzo[c][1,6]naphthyridin-6-yl)benzoic acid and [(S)-2-(3,5-dimethoxy-benzyloxy)-1-methyl-ethyl]-isopropyl-amine as described for example 1.

MS: calc.: $C_{38}H_{49}N_3O_6$ (643.83) fnd.: [M+1] 644.8

18. 4-((4aR,10bS)-9-Ethoxy-8-methoxy-2-methyl-1,2,3,4,4a,10b-hexahydro-benzo [c][1,6]naphthyridin-6-yl)-N-isopropyl-N—[(S)-1-methyl-2-(4-trifluoromethyl-benzyloxy)-ethyl]-benzamide

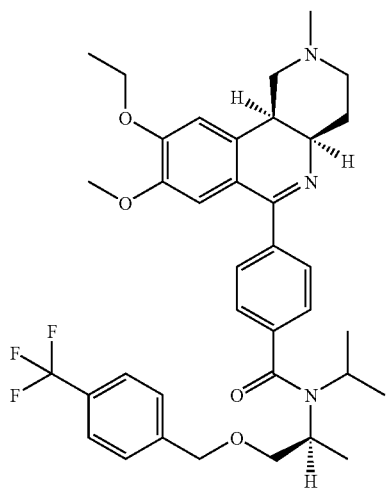

Prepared from 4-((4aR,10bS)-9-ethoxy-8-methoxy-2-methyl-1,2,3,4,4a,10b-hexahydro-benzo[c][1,6]naphthyridin-6-yl)benzoic acid and N-isopropyl-N—[(S)-1-methyl-2-(4-trifluoromethyl-benzyloxy)-ethyl]-amine as described for example 1.

MS: calc.: $C_{37}H_{44}F_3N_3O_4$ (651.78) fnd.: [M+1] 652.8

19. N—[(S)-2-(4-Cyano-benzyloxy)-1-methyl-ethyl]-4-((4aR,10bS)-9-ethoxy-8-methoxy-2-methyl-1,2,3,4,4a,10b-hexahydro-benzo[c][1,6]naphthyridin-6-yl)-N-isopropyl-benzamide

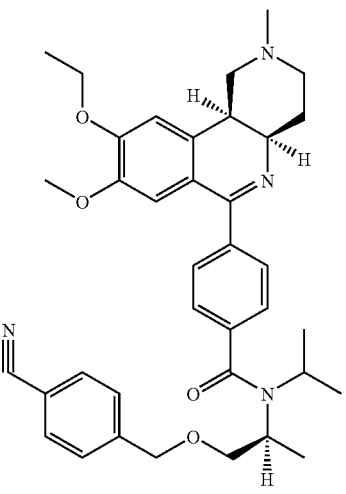

Prepared from 4-((4aR,10bS)-9-ethoxy-8-methoxy-2-methyl-1,2,3,4,4a,10b-hexahydro-benzo[c][1,6]naphthyridin-6-yl)benzoic acid and N—[(S)-2-(4-cyano-benzyloxy)-1-methyl-ethyl]-N-isopropyl-amine as described for example 1

MS: calc.: $C_{37}H_{44}N_4O_4$ (608.79) fnd.: [M+1] 609.6

20. 4-((4aR,10bS)-9-Ethoxy-8-methoxy-2-methyl-1,2,3,4,4a,10b-hexahydro-benzo [c][1,6]naphthyridin-6-yl)-N-isopropyl-N—[(S)-2-(4-methoxy-benzyloxy)-1-methyl-ethyl]-benzamide

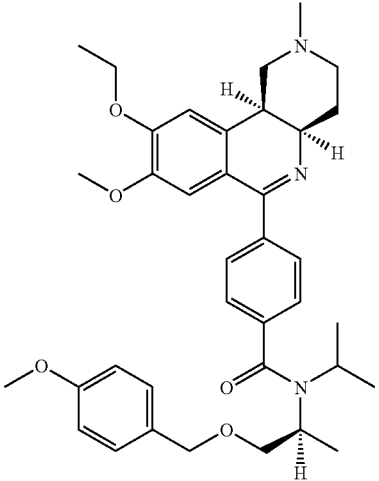

Prepared from 4-((4aR,10bS)-9-ethoxy-8-methoxy-2-methyl-1,2,3,4,4a,10b-hexahydro-benzo[c][1,6]naphthyridin-6-yl)benzoic acid and N-isopropyl-N—[(S)-2-(4-methoxy-benzyloxy)-1-methyl-ethyl]-amine as described for example 1.

MS: calc.: $C_{37}H_{47}N_3O_5$ (613.80) fnd.: [M+1] 615

21. 4-((4aR,10bS)-9-Ethoxy-8-methoxy-2-methyl-1,2,3,4,4a,10b-hexahydro-benzo [c][1,6]naphthyridin-6-yl)-N-isopropyl-N—[(S)-1-methyl-2-(3-phenyl-propoxy)-ethyl]-benzamide

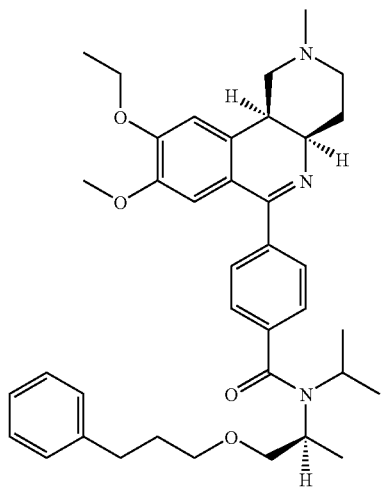

Prepared from 4-((4aR,10bS)-9-ethoxy-8-methoxy-2-methyl-1,2,3,4,4a,10b-hexahydro-benzo[c][1,6]naphthyridin-6-yl)benzoic acid and N-isopropyl-N—[(S)-1-methyl-2-(3-phenyl-propoxy)-ethyl]-amine as described for example 1.

MS: calc.: $C_{38}H_{49}N_3O_4$ (611.83) fnd.: [M+1] 612.8

22. N—((S)-1-Benzyloxymethyl-3-methyl-butyl)-4-((4aR,10bS)-9-ethoxy-8-methoxy-2-methyl-1,2,3,4,4a,10b-hexahydro-benzo[c][1,6]naphthyridin-6-yl)-N-methyl-benzamide

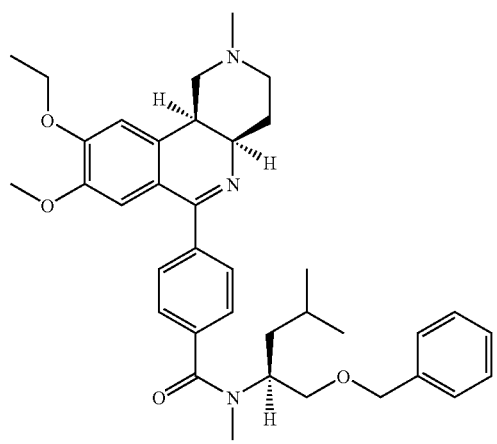

Prepared from 4-((4aR,10bS)-9-ethoxy-8-methoxy-2-methyl-1,2,3,4,4a,10b-hexahydro-benzo[c][1,6]naphthyridin-6-yl)benzoic acid and N—((S)-1-benzyloxymethyl-3-methyl-butyl)-N-methyl-amine as described for example 1.

MS: calc.: $C_{37}H_{47}N_3O_4$ (597.80) fnd.: [M+1] 599

23. N-Benzyl-N-((S)-2-benzyloxy-1-methyl-ethyl)-4-((4aR,10bS)-9-ethoxy-8-methoxy-2-methyl-1,2,3,4,4a,10b-hexahydro-benzo[c][1,6]naphthyridin-6-yl)-benzamide

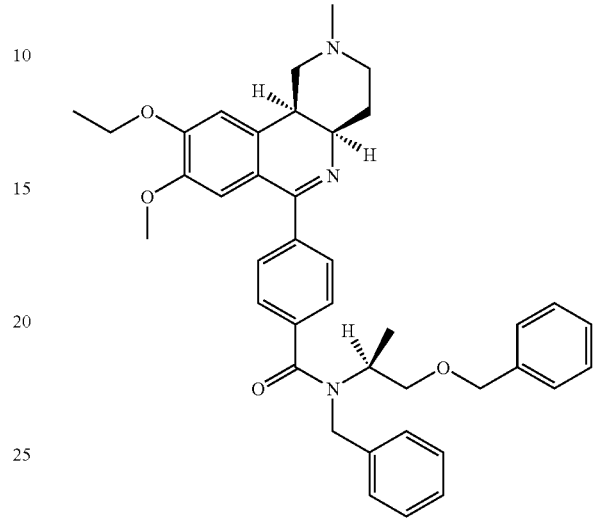

Prepared from 4-((4aR,10bS)-9-ethoxy-8-methoxy-2-methyl-1,2,3,4,4a,10b-hexahydro-benzo[c][1,6]naphthyridin-6-yl)benzoic acid and N-benzyl-N-((S)-2-benzyloxy-1-methyl-ethyl)-amine as described for example 1.

MS: calc.: $C_{40}H_{45}N_3O_4$ (631.82) fnd.: [M+1] 632.8

24. N—((S)-2-Benzyloxy-1-methyl-ethyl)-4-((4aR,10bS)-9-ethoxy-8-methoxy-2-methyl-1,2,3,4,4a,10b-hexahydro-benzo[c][1,6]naphthyridin-6-yl)-benzamide

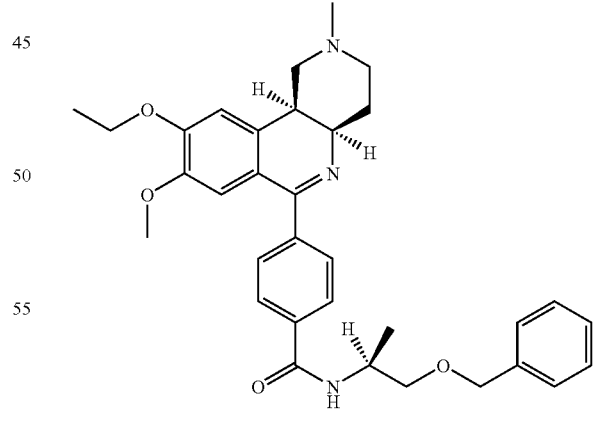

Prepared from 4-((4aR,10bS)-9-ethoxy-8-methoxy-2-methyl-1,2,3,4,4a,10b-hexahydro-benzo[c][1,6]naphthyridin-6-yl)benzoic acid and N—((S)-2-benzyloxy-1-methyl-ethyl)-amine as described for example 1.

MS: calc.: $C_{33}H_{39}N_3O_4$ (541.70) fnd.: [M+1] 542.8

Starting Materials

A. 4-((4aR,10bS)-9-Ethoxy-8-methoxy-2-methyl-1, 2,3,4,4a,10b-hexahydrobenzo[c][1,6]naphthyridin-6-yl)benzoic acid chloride dihydrochloride=4-((−)-cis-9-Ethoxy-8-methoxy-2-methyl-1,2,3,4,4a,10b-hexahydrobenzo[c][1,6]naphthyridin-6-yl)benzoic acid chloride dihydrochloride The title compound is obtained from 4-((4aR,10bS)-9-ethoxy-8-methoxy-2-methyl-1,2,3,4,4a,10b-hexahydrobenzo[c][1,6]naphthyridin-6-yl)benzoic acid by the reaction, known to the person skilled in the art, with a chlorinating agent, such as thionyl chloride, oxalyl chloride, phosphorus trichloride or phosphorus pentachloride. The resulting acid chloride is directly used for the further reaction without purification.

B. 4-((4aR,10bS)-9-Ethoxy-8-methoxy-2-methyl-1, 2,3,4,4a,10b-hexahydrobenzo[c][1,6]naphthyridin-6-yl)benzoic acid=4-((−)-cis-9-Ethoxy-8-methoxy-2-methyl-1,2,3,4,4a,10b-hexa-hydrobenzo[c][1,6]naphthyridin-6-yl)benzoic acid The title compound is prepared as described in WO98/21208;

Optical rotation: $[\alpha]_D^{20} = -109.7°$ (c=1, methanol+1.0 equivalent 0.1 N aq. sodium hydroxide)

Commercial Utility

The compounds according to the invention have valuable pharmacological properties which make them commercially utilizable. As selective inhibitors of type 3 and 4 of cyclic nucleotide phosphodiesterase (PDE3, PDE4), they are suitable on the one hand as bronchial therapeutics (for the treatment of airway obstructions on account of their dilating action and cilia-stimulating action but also on account of their respiratory rate- and respiratory drive-increasing action), but on the other hand especially for the treatment of disorders of inflammatory nature, e.g. of the airways (asthma prophylaxis), of the skin, of the intestine, of the eyes and of the joints, which are mediated by mediators such as interferons, members of the tumour necrosis factor family, interleukins, chemokines, colony-stimulating factors, growth factors, lipid mediators (e.g., inter alia, PAF, platelet-activating factor), bacterial factors (e.g. LPS), immunoglobulins, oxygen free radicals and related free radicals (e.g. nitrogen monoxide NO), biogenic amines (e.g. histamine, serotonin), kinins (e.g. bradykinin), neurogenic mediators (such as substance P, neurokinin), proteins such as, for example, granular contents of leukocytes (inter alia cationic proteins of eosinophils) and adherence proteins (e.g. integrins). The compounds according to the invention have smooth muscle-relaxant action, e.g. in the region of the bronchial system, of the blood circulation, and of the efferent urinary passages. Furthermore, they have cilia frequency-increasing action, for example in the bronchial system.

In this context, the compounds according to the invention are distinguished by low toxicity, good human acceptance, good enteral absorption and high bioavailability, great therapeutic breadth, the absence of significant side effects and good water solubility.

On account of their PDE-inhibiting properties, the compounds according to the invention can be employed as therapeutics in human and veterinary medicine, where they can be used, for example, for the treatment and prophylaxis of the following diseases: acute and chronic (in particular inflammatory and allergen-induced) respiratory disorders of various origins (bronchitis, allergic bronchitis, bronchial asthma, emphysema, COPD); disorders associated with impaired cilia function or increased demands on ciliar clearance (bronchitis, mucoviscidosis), dermatoses (especially of proliferative, inflammatory and allergic type) such as, for example, psoriasis (vulgaris), toxic and allergic contact eczema, atopic eczema, seborrheic eczema, lichen simplex, sunburn, pruritus in the anogenital area, alopecia greata, hypertrophic scars, discoid lupus erythematosus, follicular and widespread pyodermias, endogenous and exogenous acne, acne rosacea and other proliferative, inflammatory and allergic skin disorders; disorders which are based on excessive release of TNF and leukotrienes, i.e., for example, disorders of the arthritis type (rheumatoid arthritis, rheumatoid spondylitis, osteoarthritis and other arthritic conditions), systemic lupus erythematosus, disorders of the immune system (AIDS), including AIDS-related encephalopathies, autoimmune disorders such as diabetes mellitus (type I, autoimmune diabetes), multiple sclerosis and of the type virus-, bacteria- or parasite-induced demyelinization diseases, cerebral malaria or Lyme's disease, shock symptoms [septic shock, endotoxin shock, Gram-negative sepsis, toxic shock syndrome and ARDS (adult respiratory distress syndrome)] and also generalized inflammations in the gastrointestinal region (Crohn's disease and ulcerative colitis); disorders which are based on allergic and/or chronic, faulty immunological reactions in the region of the upper airways (pharynx, nose) and of the adjacent regions (paranasal sinuses, eyes), such as, for example, allergic rhinitis/sinusitis, chronic rhinitis/sinusitis, allergic conjunctivitis and also nasal polyps; and also disorders of the central nervous system such as memory disorders and Alzheimer's disease, candidiasis, leishmaniases and leprosy. In addition, the compounds of the invention are useful in the treatment of leukaemia and osteoporosis.

On account of their vasorelaxant activity, the compounds according to the invention can also be used for the treatment of high blood pressure disorders of various origins such as, for example, pulmonary high blood pressure and the concomitant symptoms associated therewith, for the treatment of erectile dysfunction or colics of the kidneys and the ureters in connection with kidney stones.

On account of their cAMP-increasing action, however, they can also be used for disorders of the heart which can be treated by PDE inhibitors, such as, for example, cardiac insufficiency, and also as anti-thrombotic, platelet aggregation-inhibiting substances.

The invention further relates to a method for the treatment of mammals including humans who are suffering from one of the abovementioned diseases. The method comprises administering a therapeutically effective and pharmacologically acceptable amount of one or more of the compounds according to the invention to the sick mammal.

The invention further relates to the compounds according to the invention for use in the treatment and/or prophylaxis of diseases, in particular the diseases mentioned.

The invention also relates to the use of the compounds according to the invention for the production of pharmaceutical compositions which are employed for the treatment and/or prophylaxis of the diseases mentioned.

The invention furthermore relates to pharmaceutical compositions for the treatment and/or prophylaxis of the diseases mentioned and which contain one or more of the compounds according to the invention.

A further subject of the invention is a commercial product, consisting of a customary secondary pack, a primary pack containing the pharmaceutical composition (for example an ampoule or a blister pack) and, if desired, an information leaflet, the pharmaceutical composition exhibiting antagonistic action against cyclic nucleotide phosphodiesterases of types 3 and 4 and leading to the attenuation of the symptoms of illnesses which are connected with cyclic nucleotide phosphodiesterases of types 3 and 4, and the suitability of the pharmaceutical composition for the prophylaxis or treatment of illnesses which are connected with cyclic nucleotide phosphodiesterases of types 3 and 4 being indicated on the secondary pack and/or on the information leaflet of the commercial product, and the pharmaceutical composition containing one or more compounds of formula 1 according to the invention. The secondary pack, the primary pack containing the pharmaceutical composition and the information leaflet otherwise comply with what would be regarded as standard to the person skilled in the art for pharmaceutical compositions of this type.

Advantageously, the substances according to the invention are also suitable for combination with other substances which bring about stimulation of CAMP, such as prostaglandins (PGE2, PGI2 and prostacyclin) and their derivatives, direct adenylate cyclase stimulators such as forskolin and related substances, or substances indirectly stimulating adenylate cyclase, such as catecholamines and adrenergic receptor agonists, in particular beta-mimetics. In combination, on account of their cAMP degradation-inhibiting action, they in this case display a synergistic, superadditive activity. This comes to bear, for example, in their use in combination with PGE2 for the treatment of pulmonary hypertension.

The pharmaceutical compositions are prepared by processes which are known per se and familiar to the person skilled in the art. As pharmaceutical compositions, the compounds according to the invention (=active compounds) are either employed as such, or preferably in combination with suitable pharmaceutical auxiliaries and/or excipients, e.g. in the form of tablets, coated tablets, capsules, caplets, suppositories, patches (e.g. as TTS), emulsions, suspensions, gels or solutions, the active compound content advantageously being between 0.1 and 95% and where, by the appropriate choice of the auxiliaries and/or excipients, a pharmaceutical administration form (e.g. a delayed release form or an enteric form) exactly suited to the active compound and/or to the desired onset of action can be achieved.

The person skilled in the art is familiar with auxiliaries or excipients which are suitable for the desired pharmaceutical formulations on account of his/her expert knowledge. In addition to solvents, gel formers, ointment bases and other active compound excipients, for example antioxidants, dispersants, emulsifiers, preservatives, solubilizers, colorants, complexing agents or permeation promoters, can be used.

The administration of the pharmaceutical compositions according to the invention may be performed in any of the generally accepted modes of administration available in the art. Illustrative examples of suitable modes of administration include intravenous, oral, nasal, parenteral, topical, transdermal and rectal delivery. Oral delivery is preferred.

For the treatment of disorders of the respiratory tract, the compounds according to the invention are preferably also administered by inhalation in the form of an aerosol; the aerosol particles of solid, liquid or mixed composition preferably having a diameter of 0.5 to 10 μm, advantageously of 2 to 6 μm.

Aerosol generation can be carried out, for example, by pressure-driven jet atomizers or ultrasonic atomizers, but advantageously by propellant-driven metered aerosols or propellant-free administration of micronized active compounds from inhalation capsules.

Depending on the inhaler system used, in addition to the active compounds the administration forms additionally contain the required excipients, such as, for example, propellants (e.g. Frigen in the case of metered aerosols), surface-active substances, emulsifiers, stabilizers, preservatives, flavorings, fillers (e.g. lactose in the case of powder inhalers) or, if appropriate, further active compounds.

For the purposes of inhalation, a large number of apparatuses are available with which aerosols of optimum particle size can be generated and administered, using an inhalation technique which is as right as possible for the patient. In addition to the use of adaptors (spacers, expanders) and pear-shaped containers (e.g. Nebulator®, Volumatic®), and automatic devices emitting a puffer spray (Autohaler®), for metered aerosols, in particular in the case of powder inhalers, a number of technical solutions are available (e.g. Diskhaler®, Rotadisk®, Turbohaler® or the inhaler described in European Patent Application EP 0 505 321), using which an optimal administration of active compound can be achieved.

For the treatment of dermatoses, the compounds according to the invention are in particular administered in the form of those pharmaceutical compositions which are suitable for topical application. For the production of the pharmaceutical compositions, the compounds according to the invention (=active compounds) are preferably mixed with suitable pharmaceutical auxiliaries and further processed to give suitable pharmaceutical formulations. Suitable pharmaceutical formulations are, for example, powders, emulsions, suspensions, sprays, oils, ointments, fatty ointments, creams, pastes, gels or solutions.

The pharmaceutical compositions according to the invention are prepared by methods known per se. The dosage of the active compounds takes place in the order of magnitude customary for PDE inhibitors. Thus topical application forms (such as, for example, ointments) for the treatment of dermatoses contain the active compounds in a concentration of, for example, 0.1-99%. The dose for administration by inhalation is customarily between 0.1 and 3 mg per day. The customary dose in the case of systemic therapy (p.o. or i.v.) is between 0.01 and 10 mg per kilogram per day.

Biological Investigations

The second messenger cyclic AMP (cAMP) is known for inhibiting inflammatory cells and cells responsible for the immunological response. The PDE4 isoenzyme is widely distributed in cells associated with the initiation and spreading of inflammatory diseases (H Tenor and C Schudt, in "Phosphodiesterase Inhibitors", 21-40, "The Handbook of Immunopharmacology", Academic Press 1996); its inhibition results in the increase of the intracellular cyclic AMP concentration and thus in the inhibition of cellular activation (J E Souness et al., Immunopharmacology 47: 127-162, 2000).

The anti-inflammatory potential of PDE4 inhibitors in vivo has been described in various animal models (MMTeixeira, TIPS 18: 164-170, 1997). To examine the PDE4 inhibition on a cellular level (in vitro), a large number of proinflammatory responses can be measured. Examples are the superoxide production of neutrophilic (C Schudt et al., Arch Pharmacol 344: 682-690, 1991) or eosinophilic (A Hatzelmann et al., Brit J Pharmacol 114: 821-831, 1995) granulocytes, which can be measured as luminol-enhanced chemiluminescence, or the synthesis of tumor necrosis factor alpha (TNFα) in monocytes, macrophages or dendritic cells (Gantner et al., Brit J Pharmacol 121: 221-231, 1997 and Pulmonary Pharmacol Therap 12: 377-386, 1999). The immunomodulatory potential of the PDE4 inhibitors furthermore becomes apparent by inhibition of T-cell responses such as cytokine synthesis or proliferation (D M Essayan, Biochem Pharmacol 57: 965-973, 1999). PDE4 inhibition by the substances according to the invention is thus a central indicator of the suppression of inflammatory processes.

Some of the cells involved in inflammatory processes contain, in addition to PDE4, also the PDE3 isoenzyme which likewise contributes to the total cAMP metabolism of these cells. Examples are endothelial cells, mast cells, T-cells, macrophages and dendritic cells. In these cell types, the inhibitory action of PDE4 inhibitors can be enhanced by additional PDE3 inhibition. In the case of (respiratory) smooth muscle cells, inhibition of the PDE3 activity is furthermore important for (broncho)relaxation (A Hatzelmann et al., in "Phosphodiesterase Inhibitors", 147-160, "The Handbook of ImmunoPharmacology", Academic Press, 1996).

Method for Measuring Inhibition of PDE3 and PDE4 Activities

Method A:

The PDE activity was determined according to Thompson et al. (Adv Cycl Nucl Res 10: 69-92, 1979) with some modifications (Bauer and Schwabe, Naunyn-Schmiedeberg's Arch Pharmacol 311: 193-198, 1980). The test samples contained 20 mM Tris (pH 7.4), 5 mM $MgCl_2$, 0.5 µM cAMP or cGMP, [$^3$H]cAMP or [$^3$H]cGMP (about 30 000 cpm/sample), the PDE isoenzyme-specific additives described in greater detail below, the indicated concentrations of inhibitor and an aliquot of the enzyme solution in a total sample volume of 200 µl. Dilution series of the compounds according to the invention were prepared in DMSO and further diluted in the samples [1:100 (v/v)], to give the desired end concentration of the inhibitors at a DMSO concentration of 1% (v/v), which for its part has only a minute effect on PDE activity.

After preincubation at 37° C. for 5 minutes, the reaction was started by addition of the substrate (cAMP or cGMP). The samples were incubated at 37° C. for a further 15 min. The reaction was terminated by addition of 50 µl 0.2 N HCl. After cooling on ice for 10 minutes and addition of 25 µg 5'-nucleotidase (snake venom from Crotalus atrox), the mixture was again incubated at 37° C. for 10 min and the samples were then applied to QAE Sephadex A-25 columns (sample volume 1 ml). The columns were eluted with 2 ml of 30 mM ammonium formate (pH 6.0). The radioactivity of the eluate was measured and corrected by the corresponding blank values (measured in the presence of denatured protein); the blank values were less than 5% of the total radioactivity. In no case did the proportion of hydrolyzed nucleotide exceed 30% of the original substrate concentration.

PDE3 (cGMP-inhibited) was investigated in homogenates of human platelets (see Schudt et al., Biochem Pharmacol 1991: 42, 153-162) using cAMP or cGMP as substrate.

PDE4 (cAMP-specific) was investigated in the cytosol of human polymorphonuclear leukocytes (PMNL) [isolated from leukocyte concentrates, see Schudt et al., Arch Pharmacol 1991: 344, 682-690] using cAMP as substrate. The PDE3 inhibitor motapizone (1 µM) was used to suppress the PDE3 activity emanating from contaminated platelets.

The $IC_{50}$ values were determined from the concentration-inhibition curves by nonlinear regression.

Method B:

The cDNA for PDE3A1 (GB no. U36798) was isolated in 2 steps using PCR. A 3' terminal cDNA fragment of PDE3A1 was amplified from fat cells cDNA (Clontech, Palo Alto) using primers OZ 458 (5'-AAAGTCGACTCACTGGTCTG-GCTTTTGG-3') and OZ 457 (5'-GTCGACCAGGTGC-CCTCGCTA-3'). The 5' terminal cDNA fragment of PDE3A1 was amplified from Placenta cDNA (Clontech, Palo Alto) using primers OZ 455 (5'-ATGGCAGTGCCCGGC-GACGCT-3') and OZ 456 (5'-GTCGACTTTGCTTTT-TAGCCT-3'). The PCR products were cloned into pCR2.1-Topo (Invitrogen, Groningen, NL) under standard conditions (the manufacturer's instructions). The 3' fragment was cut out with HindII and cloned into the HindII site of the construct carrying the 5' fragment. The whole ORF was subcloned into pBacPak9 (Clontech, Palo Alto) using EcoRI. Aminoacid 12 is Aspartic Acid like in sequence GB no. AJ005036, aa 69 and aa 110 are respective Serine and Glycine like in both sequences GB no. AJ005036 and GB no. M91667.

The PDE4B2 (GB no. M97515) was a gift of Prof. M. Conti (Stanford University, USA). It was amplified from the original plasmid (pCMV5) via PCR with primers Rb9 (5'-GC-CAGCGTGCAAATAATGAAGG-3') and Rb10 (5'-AGAGGGGGATTATGTATCCAC-3') and cloned into the pCR-Bac vector (Invitrogen, Groningen, NL).

The recombinant baculovirus was prepared by means of homologous recombination in SF9 insect cells. The expression plasmids were cotransfected with Bac-N-Blue (Invitrogen, Groningen, NL) or Baculo-Gold DNA (Pharmingen, Hamburg) using a standard protocol (Pharmingen, Hamburg). Wt virus-free recombinant virus supernatants were selected using plaque assay methods. After that, high-titre virus supernatants were prepared by amplifying 3 times. PDEs were expressed in SF21 cells by infecting $2 \times 10^6$ cells/ml with an MOI (multiplicity of infection) between 1 and 10 in serum-free SF900 medium (Life Technologies, Paisley, UK). The cells were cultured at 28° C. for 48-72 hours, after which they were pelleted for 5-10 min at 1000 g and 4° C.

The SF21 insect cells were resuspended, at a concentration of approx. $10^7$ cells/ml, in ice-cold (4° C.) homogenization buffer (20 mM Tris, pH 8.2, containing the following additions: 140 mM NaCl, 3.8 mM KCl, 1 mM EGTA, 1 mM $MgCl_2$, 10 mM β-mercaptoethanol, 2 mM benzamidine, 0.4 mM Pefablock, 10 µM leupeptin, 10 µM pepstatin A, 5 µM trypsin inhibitor) and disrupted by ultrasonication. The homogenate was then centrifuged for 10 min at 1000×g and the supernatant was stored at −80° C. until subsequent use (see below). The protein content was determined by the Bradford method (BioRad, Munich) using BSA as the standard.

PDE3A1 and PDE4B2 activities were inhibited by the said compounds in a modified SPA (scintillation proximity assay) test, supplied by Amersham Biosciences (see procedural instructions "phosphodiesterase [3H]cAMP SPA enzyme assay, code TRKQ 7090"), carried out in 96-well microtitre plates (MTP's). The test volume is 100 µl and contains 20 mM Tris buffer (pH 7.4), 0.1 mg of BSA (bovine serum albumin)/ml, 5 mM $Mg^{2+}$, 0.5 µM cAMP (including about 50,000 cpm of [3H]cAMP), 1 µl of the respective substance dilution in DMSO and sufficient recombinant PDE (1000×g supernatant, see above) to ensure that 10-20% of the cAMP is converted under the said experimental conditions. The final concentration of DMSO in the assays (1% v/v) does not substantially affect the activity of the PDEs investigated. After a preincubation of 5 min at 37° C., the reaction is started by adding the substrate (cAMP) and the assays are incubated for a further 15 min; after that, they are stopped by adding SPA beads (50 µl). In accordance with the manufacturer's instructions, the SPA beads had previously been resuspended in water, but were then diluted 1:3 (v/v) in water; the diluted solution also contains 3 mM IBMX to ensure a complete PDE activity stop. After the beads have been sedimented (>30 min), the MTP's are analyzed in commercially available luminescence detection devices. The corresponding $IC_{50}$ values of the compounds for the inhibition of PDE activities are determined from the concentration-effect curves by means of non-linear regression.

The inhibitory values determined for the compounds according to the invention follow from the following Table 1, in which the numbers of the compounds correspond to the numbers of the examples.

The inhibitory values of the compounds 1-16 and 22-24 have been determined according to Method A. The inhibitory values of the compounds 17-21 have been determined according to Method B.

TABLE 1

| Compound | PDE4 [$-\log IC_{50}$, mol/l] | PDE3 |
|---|---|---|
| 1 | 8.9 | 6.2 |
| 2 | 8.5 | 5.8 |
| 3 | 9.0 | 6.0 |
| 4 | 8.4 | 6.1 |
| 5 | 8.9 | 6.7 |
| 6 | 9.2 | 6.9 |
| 7 | 8.8 | 7.1 |
| 8 | 9.8 | 7.5 |
| 9 | 9.8 | 7.8 |
| 10 | 8.9 | 7.0 |
| 11 | 9.0 | 7.1 |
| 12 | 9.4 | 6.8 |
| 13 | 9.9 | 6.7 |
| 14 | 7.8 | 6.0 |
| 15 | 8.0 | 6.6 |
| 16 | 8.5 | 6.4 |
| 17 | 9.5 | 7.4 |
| 18 | 9.0 | 7.1 |
| 19 | 9.4 | 7.6 |
| 20 | 9.5 | 7.4 |
| 21 | 8.7 | 7.4 |
| 22 | 9.4 | 7.2 |
| 23 | 9.5 | 6.8 |
| 24 | 9.0 | 6.6 |

The invention claimed is:

1. A compound of formula 1,

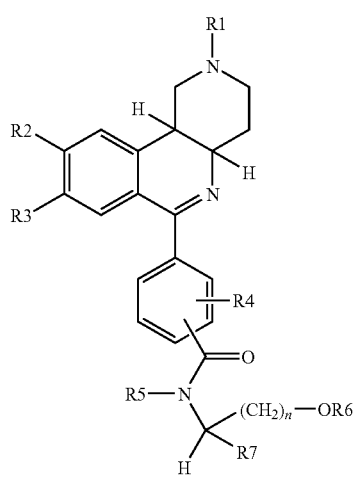

(1)

in which

R1 is 1-4C-alkyl,

R2 is 1-2C-alkoxy, 3-5C-cycloalkoxy, 3-5C-cycloalkylmethoxy, or 1-2C-alkoxy which is completely or predominantly substituted by fluorine, R3 is 1-2C-alkoxy, 3-5C-cycloalkoxy, 3-5C-cycloalkylmethoxy, or 1-2C-alkoxy which is completely or predominantly substituted by fluorine, R4 is hydrogen, 1-4C-alkyl, trifluoromethyl or 1-4C-alkoxy, R5 is hydrogen, 1-4C-alkyl, 3-7C-cycloalkyl or phenyl-1-4C-alkyl, R6 is 1-4C-alkyl, phenyl-1-4C-alkyl, or Aryl-1-4C-alkyl, in which Aryl is R61- and/or R62-substituted phenyl, in which R61 is 1-4C-alkoxy, trifluoromethyl or cyano, R62 is 1-4C-alkoxy, R7 is hydrogen or 1-4C-alkyl, n is 1 or 2, or a salt, N-oxide or salt of an N-oxide thereof.

2. A compound of formula 1 according to claim 1 in which

R1 is methyl,

R2 is 1-2C-alkoxy,

R3 is 1-2C-alkoxy,

R4 is hydrogen,

R5 is hydrogen, 1-4C-alkyl, 3-7C-cycloalkyl or phenyl-1-4C-alkyl,

R6 is 1-4C-alkyl, phenyl-1-4C-alkyl, or Aryl-1-4C-alkyl, in which

Aryl is 1-4C-alkoxy-substituted phenyl, trifluoromethyl-substituted phenyl, cyano-substituted phenyl, or R61- and R62-substituted phenyl, in which R61 is 1-4C-alkoxy, R62 is 1-4C-alkoxy, and in which either R7 is hydrogen or 1-4C-alkyl, n is 1 or 2, or a salt, N-oxide or salt of an N-oxide thereof.

3. A compound of formula 1 according to claim 1 in which

R1 is methyl,

R2 is ethoxy,

R3 is methoxy,

R4 is hydrogen,

R5 is hydrogen, methyl, ethyl, propyl, isopropyl, cyclohexyl or benzyl,

R6 is methyl, ethyl, isopropyl, butyl, benzyl, 3-phenylpropyl, or Aryl-methyl, in which Aryl is 4-methoxyphenyl, 4-trifluoromethyiphenyl, 4-cyanophenyl or 3,5-dimethoxyphenyl, and in which either R7 is hydrogen or methyl, and n is 1 or 2, or R7 is ethyl or isobutyl, and n is 1, or a salt, N-oxide or salt of an N-oxide thereof.

4. A compound of formula 1 according to claim 1, in which the hydrogen atoms in positions 4a and 10b are in the cis position relative to one another, or a salt, N-oxide or salt of an N-oxide thereof.

5. A compound of formula 1 according to claim 1, which have with respect to the chiral centers, the configuration shown in formulae (1*) or (1**):

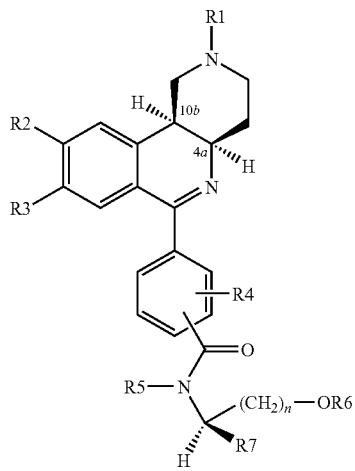

(1*)

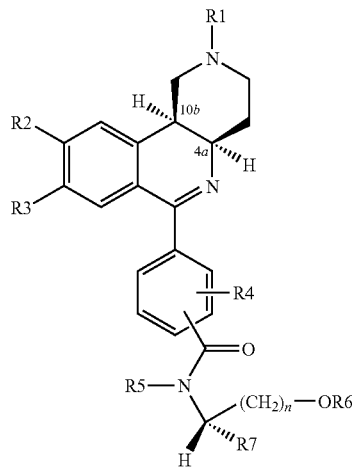

(1**)

or a salt, N-oxide or salt of an N-oxide thereof.

6. A pharmaceutical composition comprising one or more compounds of formula 1 as claimed in claim 1, or a pharmaceutically acceptable salt, N-oxide or salt of an N-oxide thereof, together with a pharmaceutically acceptable auxiliary and/or excipient.

* * * * *

UNITED STATES PATENT AND TRADEMARK OFFICE
CERTIFICATE OF CORRECTION

PATENT NO. : 7,671,068 B2  Page 1 of 1
APPLICATION NO. : 10/591955
DATED : March 2, 2010
INVENTOR(S) : Dieter Flockerzi It is certified that error appears in the above-identified patent and that said Letters Patent is hereby corrected as shown below:

Column 30, Claim 3, Line 55

Please delete "4-trifluoromethyiphenyl"

and replace with -- 4-trifluoromethylphenyl --

Signed and Sealed this

Eleventh Day of May, 2010

David J. Kappos
*Director of the United States Patent and Trademark Office*